United States Patent [19]
Berg et al.

[11] Patent Number: 4,935,103
[45] Date of Patent: * Jun. 19, 1990

[54] SEPARATION OF N-PROPANOL FROM T-AMYL ALCOHOL BY EXTRACTIVE DISTILLATION

[75] Inventors: Lloyd Berg, 1314 S. Third Ave., Bozeman, Mont. 59715; Robert W. Christensen, Bozeman, Mont.

[73] Assignee: Lloyd Berg, Bozeman, Mont.

[*] Notice: The portion of the term of this patent subsequent to Dec. 1, 2004 has been disclaimed.

[21] Appl. No.: 419,541

[22] Filed: Oct. 10, 1989

[51] Int. Cl.$^5$ .................... B01D 3/40; C07C 29/84
[52] U.S. Cl. ................................. 203/60; 203/51; 203/56; 203/57; 203/61; 203/64; 203/65; 568/913
[58] Field of Search ................... 203/51, 60, 61, 62, 203/58, 65, 63, 64; 568/913, 918

[56] References Cited
U.S. PATENT DOCUMENTS

| | | | |
|---|---|---|---|
| 2,570,205 | 10/1951 | Carlson et al. | 203/58 |
| 2,575,243 | 11/1951 | Carlson et al. | 203/60 |
| 2,591,712 | 4/1952 | Morrell et al. | 203/84 |
| 2,591,713 | 4/1952 | Morrell et al. | 203/84 |
| 4,710,274 | 12/1987 | Berg et al. | 203/60 |
| 4,710,275 | 12/1987 | Berg et al. | 203/60 |
| 4,715,933 | 12/1987 | Berg et al. | 203/60 |
| 4,732,653 | 3/1988 | Berg et al. | 203/60 |
| 4,756,803 | 7/1988 | Berg | 203/60 |

Primary Examiner—Wilbur Bascomb

[57] ABSTRACT n-Propanol and t-amyl alcohol cannot be separated from each other by distillation because of the proximity of their boiling points. n-Propanol can be readily separated from t-amyl alcohol by using extractive distillation in which the extractive agent is a higher boiling organic compound or a mixture of two or more of these. Typical examples of effective agents are: methyl salicylate; benzyl benzoate and hexahydrophthalic anhydride; methyl salicylate, benzoic acid and hexahydrophthalic anhydride.

1 Claim, No Drawings

SEPARATION OF N-PROPANOL FROM T-AMYL ALCOHOL BY EXTRACTIVE DISTILLATION

This is a substitute application 07/210,329, abandoned.

FIELD OF THE INVENTION

This invention relates to a method for separating n-propanol from t-amyl alcohol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

n-Propanol and t-amyl alcohol are two of the most widely used alcohols in commerce today. When they are used as solvents, they frequently end up as a mixture of solvents. Whenever practical, it is mandatory to recover the solvent and re-use it.

t-Amyl alcohol boils at 102.4° C., n-propanol at 97.2° C. and these two have a relative volatility of 1.20, making it difficult to separate these two by rectification. Extractive distillation would be an attractive method of effecting the separation of n-propanol from t-amyl alcohol if agents can be found that (1) will alter the relative volatility between n-propanol and t-amyl alcohol, (2) form no azeotropes with n-propanol or t-amyl alcohol and (3) are easy to recover from t-amyl alcohol, that is boil sufficiently above t-amyl alcohol to make the separation by rectification possible with only a few theoretical plates. Extractive distillation typically requires the addition of an equal amount to twice as much extractive agent as the ethanol—isopropanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the isopropanol otherwise it will form a two phase azeotrope with it and some other method of separation will have to be employed.

TABLE 1

Effect of Relative Volatility on the Separation of n-Propanol From t-Amyl Alcohol at 99% Purity.

| Relative Volatility | Theoretical Plates | Actual Plates, 75% Efficiency | Actual Plates, 75% Eff., Min. Reflux |
| --- | --- | --- | --- |
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. When ordinary rectification is used, 87 actual plates of 75% efficiency are required at minimum reflux ratio to separate n-propanol from t-amyl alcohol in 99% purity. If extractive distillation is employed with an agent that converts the relative volatility to 1.7, only 29 actual plates are required.

A number of investigators have reported the separation of lower boiling alcohols, one from another, by extractive distillation. Carlson, U.S. Pat. No. 2,570,205 used sulfolane to separate n-propanol from butyl alcohols. Carlson, U.S. Pat. No. 2,551,584 used water in a steam distillation on a mixture of lower alcohols but was unable to separate the t-amyl alcohol from isobutanol. They remained in the same fraction. Drout, U.S. Pat. No. 2,552,412 used ethylene glycol, 1,3-propanediol and diethylene glycol as the agents in separating a mixture containing ethanol, sec. butanol, sec. amyl alcohol and t-amyl alcohols. Smith, U.S. Pat. No. 2,559,519 used glycol ethers to separate alcohol mixtures contaning ethanol, propanol, isopropanol, and sec. butanol. Smith, U.S. Pat. No. 2,559,520 used ethylene glycol and 1,3-butylene glycol as the extractive agent to separate n-propanol from sec. butanol. Carlson, U.S. Pat. No. 2,575,243 used glycol ether-esters as the agent to separate n-propanol from sec. butanol. Morrell, U.S. Pat. No. 2,591,712 used paraffinic, naphthenic or aromatic hydrocarbon oils to separate close boiling anhydrous alcohols. Morrell, U.S. Pat. No. 2,591,713 used water and a white oil to separate the lower alcohols. Morrell, U.S. Pat. No. 2,706,707 used aqueous solutions of sodium xylene sulfonate or sodium p-cymene sulfonate in the separation of lower alcohols.

OBJECTIVE OF THE INVENTION

The object of this invention is to provide a process or method of extractive distillation that will enhance the relative volatility of n-propanol from t-amyl alcohol in their separation in a rectification column. It is a further objective of this invention to identify organic compounds which are stable, can be separated from t-amyl alcohol by rectification with relatively few plates and can be recycled to the extractive distillation column and re-used with little decomposition.

SUMMARY OF THE INVENTION

The objects of this invention are provided by a process for separating n-propanol from t-amyl alcohol which entails the use of certain organic compounds as the agent in extractive distillation.

DETAILED DESCRIPTION OF THE INVENTION

We have discovered that certain benzoates, either singly or in mixtures, will effectively enhance the relative volatility between n-propanol and t-amyl alcohol and permit the separation of pure n-propanol from t-amyl alcohol by rectification when employed as the agent in extractive distillation. Table 2 lists several benzoates, their mixtures and the approximate proportions that we have found to be effective. The data in Table 2 was obtained in a vapor-liquid equilibrium still. In each case, the starting material was a 50-50% n-propanol-t-amyl alcohol mixture. The ratios are the parts of extractive agent used per part of n-propanol-t-amyl alcohol mixture. The relative volatilities are listed for each of the two ratios employed. The compounds that are effective when used alone are methyl benzoate, butyl benzoate, benzyl benzoate, diethylene glycol dibenzoate, dipropylene glycol dibenzoate and methyl o-hydroxybenzoate (methyl salicylate). The compounds which are effective when used in mixtures of two or more components with benzoates are benzoic acid, cinnamic acid, salicylic acid, sulfolane, benzyl p-hydroxybenzoate, phthalic anhydride, hexahydrophthalic anhydride, methyl hexahydrophthalic anhydride, trimellitic anhydride, tri-2-ethyl hexyl trimellitate, 2-nitrotoluene and 3,3',4,4'-benzophenone tetracarboxylic dianhydride.

TABLE 2

| Extractive Distillation Agents Which Contain Benzoates | | | | |
|---|---|---|---|---|
| Compounds | Ratios | | Relative Volatilities | |
| None | — | | 1.20 | |
| Methyl benzoate (MeBn) | 1 | 6/5 | 1.5 | 1.6 |
| Methyl benzoate, Benzoic acid | $(\frac{1}{2})^2$ | $(3/5)^2$ | 1.5 | 1.5 |
| Methyl benzoate, Benzyl p-hydroxybenzoate | " | " | 1.4 | 1.4 |
| Methyl benzoate, Cinnamic acid | " | " | 1.4 | 1.5 |
| Methyl benzoate, Dipropylene glycol dibenzoate | " | " | 1.4 | 1.4 |
| Methyl benzoate, Hexahydrophthalic anhydride | " | " | 1.6 | 1.7 |
| Methyl benzoate, Methyl hexahydrophthalic anhydride | " | " | 1.5 | 1.5 |
| Methyl benzoate, Salicylic acid | " | " | 1.5 | 1.5 |
| Methyl benzoate, Sulfolane | " | " | 1.3 | 1.4 |
| Methyl benzoate, Trimellitic anhydride | " | " | 1.4 | 1.5 |
| MeBn, Benzoic acid, Cinnamic acid | $(\frac{1}{3})^3$ | $(2/5)^3$ | 1.5 | 1.5 |
| MeBn, Benzoic acid, Benzyl p-hydroxybenzoate | " | " | 1.4 | 1.5 |
| MeBn, Benzoic acid, Hexahydrophthalic anhydride | " | " | 1.5 | 1.5 |
| MeBn, Benzoic acid, Methyl hexahydrophthalic anhyd. | " | " | 1.5 | 1.6 |
| MeBn, Benzyl benzoate, Methyl salicylate | " | " | 1.3 | 1.4 |
| MeBn, Cinnamic acid, Hexahydrophthalic anhydride | " | " | 1.5 | 1.5 |
| MeBn, Cinnamic acid, Methyl hexahydrophthalic anhyd. | " | " | 1.4 | 1.4 |
| MeBn, Benzoic acid, Methyl hexahydrophthalic anhyd. | " | " | 1.6 | 1.7 |
| MeBn, Salicylic acid, Hexahydrophthalic anhydride | " | " | 1.5 | 1.6 |
| MeBn, Salicylic acid, Methyl hexahydrophthalic anhyd. | " | " | 1.5 | 1.6 |
| MeBn, Methyl salicylate, Phthalic anhydride | " | " | 1.5 | 1.4 |
| MeBn, Methyl salicylate, Methyltetrahydrophthalic anh. | " | " | 1.5 | 1.5 |
| MeBn, Methyl salicylate, Trimellitic anhydride | " | " | 1.5 | 1.4 |
| Butyl benzoate | 1 | 6/5 | 1.2 | 1.4 |
| Butyl benzoate, Benzoic acid | $(\frac{1}{2})^2$ | $(3/5)^2$ | 1.5 | 1.5 |
| Butyl benzoate, Diethylene glycol dibenzoate | " | " | 1.5 | 1.6 |
| Butyl benzoate, Methyl salicylate | " | " | 1.5 | 1.3 |
| Butyl benzoate, Methyl salicylate, Diethylene glycol dibenzoate | $(\frac{1}{3})^3$ | $(2/5)^3$ | 1.5 | 1.6 |
| Butyl benzoate, Methyl salicylate, Salicylic acid | " | " | 1.4 | 1.5 |
| Butyl benzoate, Benzoic acid, Hexahydrophthalic anh. | " | " | 1.5 | 1.6 |
| Benzyl benzoate | 1 | — | 1.4 | — |
| Benzyl benzoate Benzoic acid | $(\frac{1}{2})^2$ | $(3/5)^2$ | 1.5 | 1.5 |
| Benzyl benzoate, Methyl salicylate | " | " | 1.5 | 1.4 |
| Benzyl benzoate, Hexahydrophthalic anhydride | " | " | 1.4 | 1.4 |
| Benzyl benzoate, Hexahydrophthalic anhydride Cinnamic acid | $(\frac{1}{3})^3$ | $(2/5)^3$ | 1.5 | 1.5 |
| Benzyl benzoate, Hexahydrophthalic anhydride, Benzoic acid | " | " | 1.4 | 1.4 |
| Diethylene glycol dibenzoate | 1 | 6/5 | 1.3 | 1.3 |
| Dipropylene glycol dibenzoate | " | " | 1.4 | 1.4 |

TABLE 3

| Extractive Distillation Agents Which Contain Methyl o-Hydroxybenzoates (also named Methyl salicylate) | | | | |
|---|---|---|---|---|
| Compounds | Ratios | | Relative Volatilities | |
| Methyl salicylate (MeSal) | 1 | 6/5 | 1.6 | 1.6 |
| MeSal, Adiponitrile | $(\frac{1}{2})^2$ | $(3/5)^2$ | 1.4 | 1.4 |
| MeSal, Benzoic acid | " | " | 1.5 | 1.5 |
| MeSal, Cinnamic acid | " | " | 1.6 | 1.6 |
| MeSal, Diethylene glycol dibenzoate | " | " | 1.4 | 1.4 |
| MeSal, Dipropylene glycol dibenzoate | " | " | 1.5 | 1.5 |
| MeSal, Phthalic anhydride | " | " | 1.4 | 1.5 |

TABLE 3-continued

Extractive Distillation Agents Which Contain Methyl o-Hydroxybenzoates
(also named Methyl salicylate)

| Compounds | Ratios | | Relative Volatilities | |
|---|---|---|---|---|
| MeSal, Hexahydrophthalic anhydride | " | " | 1.5 | 1.5 |
| MeSal, Methyl hexahydrophthalic anhydride | " | " | 1.5 | 1.5 |
| MeSal, Methyl tetrahydrophthalic anhydride | " | " | 1.4 | 1.4 |
| MeSal, Salicylic acid | " | " | 1.5 | 1.6 |
| MeSal, Trimellitic anhydride | " | " | 1.4 | 1.5 |
| MeSal, Tri-2-ethyl hexyl trimellitate | " | " | 1.5 | 1.6 |
| MeSal, Hexahydrophthalic anhydride, Benzoic acid | (⅓)³ | (2/5)³ | 1.5 | 1.5 |
| MeSal, Hexahydrophthalic anhydride, Diethylene glycol dibenzoate | " | " | 1.4 | 1.5 |
| MeSal, Hexahydrophthalic anhydride, Salicyclic acid | " | " | 1.5 | 1.6 |
| MeSal, Hexahydrophthalic anhydride, BTDA* | " | " | 1.4 | 1.4 |
| MeSal, Methyl hexahydrophthalic anhydride, Cinnamic acid | " | " | 1.4 | 1.5 |
| MeSal, Methyl hexahydrophthalic anhydride, Trimellitic anhydride | " | " | 1.4 | 1.3 |
| MeSal, Methyl hexahydrophthalic anhydride, Benzoic acid | " | " | 1.5 | 1.5 |
| MeSal, Benzoic acid, Tri-2-Ethyl hexyl mellitate | " | " | 1.4 | 1.5 |
| MeSal, Benzoic acid, Phthalic anhydride | " | " | 1.4 | 1.4 |
| MeSal, Benzoic acid, Dipropylene glycol dibenzoate | " | " | 1.5 | 1.5 |
| MeSal, BTDA*, 2-Nitrotoluene | " | " | 1.4 | 1.5 |

Note:
BTDA is 3,3',4,4''-Benzophenone tetracarboxylic dianhydride.

TABLE 4

Data From Runs Made In Rectification Column.

| Agent | Time Hrs. | Stillpot Temp. °C. | | Overhead Temp. When Sampling | Wt. % n-Propanol | | Relative Volatility |
|---|---|---|---|---|---|---|---|
| | | At Start | Sampling | | Overhead | Bottoms | |
| None | 2 | | 115 | 90 | 62 | 42 | 1.20 |
| Methyl benzoate | 0.5 | 115 | 130 | 93 | 64 | 36.5 | 1.29 |
| Methyl benzoate | 1.5 | 115 | 140 | 95 | 64.5 | 33 | 1.38 |
| Methyl benzoate | 2.0 | 115 | 150 | 95 | 65 | 27 | 1.43 |
| Methyl benzoate | 2.5 | 115 | 158 | 92 | 65.2 | 25.3 | 1.46 |
| Methyl benzoate | 3.0 | 115 | 160 | 87 | 64.8 | 26.7 | 1.43 |
| 50% MeBn, 50% HHPhAnh. | 0.5 | 105 | 160 | 74 | 66 | 35 | 1.33 |
| 50% MeBn, 50% HHPhAnh. | 1.0 | 105 | 190 | 43 | 65 | 34 | 1.33 |

Notes:
Agent feed rate; 20 ml/min; Agent temp.: 85° C.; Boilup rate: 10-20 ml/min.

The ratios in Tables 2 and 3 are the parts of extractive agent used per part of n-propanol-t-amyl alcohol mixture. The two relative volatilities correspond to the two different ratios. For example in Table 2, one part of methyl benzoate with one part of the n-propanol-t-amyl alcohol mixture gives a relative volatility of 1.5, 6/5 parts of methyl benzoate gives 1.6. One half part of butyl benzoate mixed with one half part of benzoic acid with one part of n-propanol-t-amyl alcohol mixture gives a relative volatility of 1.5, 3/5 parts of butyl benzoate plus 3/5 parts of benzoic acid gives 1.5. One third parts of methyl benzoate plus ⅓ parts of benzoic acid plus ⅓ parts of hexahydrophthalic anhydride mixed with one part of n-propanol-t-amyl alcohol mixture gives a relative volatility of 1.6, with 2/5 parts these three give 1.7. In every example in Table 2 and 3, the starting material is a 50-50% mixture of n-propanol-t-amyl alcohol which possesses a relative volatility of 1.20.

Methyl benzoate listed in Table 2 and whose relative volatility had been determined in the vapor-liquid equilibrium still, was then evaluated in a glass perforated plate rectification column possessing 4.5 theoretical plates. The results are listed in Table 4. The n-propanol-t-amyl alcohol mixture used contained about 50% t-amyl alcohol. The first run is with no extractive agent and with 400 grams of mixture in the stillpot. After two hours of operation, the separation is that in accordance with the relative volatility of 1.20. The second run is with methyl benzoate as the extractive agent. After one-half hour of continuous oprration, the relative volatility was 1.29; after 1.5 hours, 1.38; after two hours, 1.43; after 2.5 hours, 1.46; and after three hours, 1.43. Experience has shown that three or more hours of steady operation are required to reach equilibrium. The relative volatility attained, 1.46, can be compared with the 1.5 obtained for methyl benzoate with the vapor-liquid equilibrium still listed in Table 2.

THE USEFULNESS OF THE INVENTION

The usefulness or utility of this invention can be demonstrated by referring to the data presented in Tables 1, 2, and 4. All of the successful extractive distillation agents show that n-propanol can be removed from t-amyl alcohol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity n-propanol from any mixture with t-amyl alcohol. The stability of the compounds used and the boiling point difference is such that complete recovery and recycle is obtainable by a simple distillation and the amount required for make-up is small.

WORKING EXAMPLES

Example 1

Thirty grams of n-propanol, 20 grams of t-amyl alcohol and 50 grams of methyl benzoate were charged to an Othmer type glass vapor-liquid equilibrium still and refluxed for five hours. Analysis of the vapor and liquid by gas chromatography gave a vapor composition of 73.2% n-propanol, 26.8% t-amyl alcohol; a liquid composition of 64% n-propanol, 36% t-amyl alcohol. This indicates a relative volatility of 1.53. Ten grams of methyl benzoate were added and refluxing continued for another six hours. Analysis indicated a vapor composition of 73.9% n-propanol, 26.1% t-amyl alcohol; a liquid composition of 63.4% n-propanol, 36.6% t-amyl alcohol which is a relative volatility of 1.64.

Example 2

Thirty grams of n-propanol, 20 grams of t-amyl alcohol, 25 grams of methyl benzoate and 25 grams of hexahydrophthalic anhydride were charged to the vapor-liquid equilibrium still and refluxed for 12 hours. Analysis indicated a vapor composition of 70.6% n-propanol, 29.4% t-amyl alcohol; a liquid composition of 59.6% n-propanol, 40.4% t-amyl alcohol which is a relative volatility of 1.63. Five grams of methyl benzoate and five grams of hexahydrophthalic anhydride were added and refluxing continued for another eight hours. Analysis indicated a vapor composition of 68.8% n-propanol, 31.2% t-amyl alcohol; a liquid composition 55.6% n-propanol, 44.4% t-amyl alcohol which is a relative volatility of 1.76.

Example 3

Twenty grams of n-propanol, 30 grams of t-amyl alcohol, 17 grams of methyl benzoate, 17 grams of benzoic acid and 17 grams of methyl hexahydrophthalic anhydride were charged to the vapor-liquid equilibrium still and refluxed for 12 hours. Analysis indicated a vapor composition of 50.2% n-propanol, 49.8% t-amyl alcohol; a liquid composition of 38.2% n-propanol, 61.8% t-amyl alcohol which is a relative volatility of 1.63. Three grams each of methyl benzoate, benzoic acid and methyl hexahydrophthalic anhydride were added and refluxing continued for another 11 hours. Analysis indicated a vapor composition of 45.5% n-propanol, 54.5% t-amyl alcohol; a liquid composition of 32% n-propanol, 68% t-amyl alcohol which is a relative volatility of 1.71.

Example 4

A glass perforated plate rectification column was calibrated with ethylbenzene and p-xylene which possesses a relative volatility of 1.06 and found to have 4.5 theoretical plates. A solution of 100 grams of n-propanol and 100 grams of t-amyl alcohol was placed in the stillpot and heated. The column was operated at total reflux for two hours to establish equilibrium throughout. Overhead and bottoms samples of approximately 2 ml. were collected and analysed by gas chromatography. The overhead analysis was 62% n-propanol, 38% t-amyl alcohol and the stillpot analysis was 42% n-propanol and 58% t-amyl alcohol. Using these compositions in the Fenske equation with the number of theoretical plates in the column being 4.5, gave an average relative volatility of 1.20 for each theoretical plate. An extractive agent consisting of methyl benzoate was then pumped into the column at a rate of 20 ml/min. The temperature of the extractive agent as it entered the column was 85° C. After establishing the feed rate of the extractive agent, the heat input to the n-propanol-t-amyl alcohol in the stillpot was adjusted to give a reflux rate of 10–20 ml/min. After one half hour of operation, overhead and bottoms samples were collected and analysed. The overhead analysis was 64% n-propanol, 36% t-amyl alcohol and the bottoms analysis was 36.5% n-propanol, 63.5% t-amyl alcohol which gave an average relative volatility of 1.29 for each theoretical plate. After 1.5 hours of total operating time, the overhead and bottoms samples were again taken and analysed. The overhead composition was 64.5% n-propanol, 35.5% t-amyl alcohol and the bottoms composition was 33% n-propanol, 67% t-amyl alcohol. This gave an average relative volatility of 1.38 for each theoretical plate. After two hours of total operating time, the overhead and bottoms samples were again taken and analysed. The overhead composition was 65% n-propanol, 35% t-amyl alcohol and the bottoms composition was 27% n-propanol, 73% t-amyl alcohol. This gave an average relative volatility 1.43 for each theoretical plate. After 2.5 hours of total operating time, the overhead analysed 65.2% n-propanol, 34.8% t-amyl alcohol and the bottoms analysed 25.3% n-propanol, 74.7% t-amyl alcohol which is an average relative volatility of 1.46 for each theoretical plate. After three hours of total operating time, the overhead analysed 64.8% n-propanol, 35.2% t-amyl alcohol and the bottoms analysed 26.7% n-propanol, 73.3% t-amyl alcohol which is an average relative volatility of 1.43 for each theoretical plate. The data in this example are summarized in Table 4.

We claim:

1. A method for recovering n-propanol from a mixture of n-propanol and t-amyl alcohol which comprises distilling a mixture of n-propanol and t-amyl alcohol in the presence of about one part of an extractive agent per part of n-propanol-t-amyl alcohol mixture, recovering n-propanol as overhead product and obtaining the extractive agent and the t-amyl alcohol from the stillpot, the extractive agent comprises diethylene glycol dibenzoate.

* * * * *